(12) United States Patent
Pollack et al.

(10) Patent No.: US 7,030,248 B2
(45) Date of Patent: *Apr. 18, 2006

(54) ISOLATION OF NATURAL L-β-3-INDOLYLALANINE AND ENRICHMENT OF NATURAL ALIPHATIC AMINO ACID MIXTURES WITH NATURAL L-β-3-INDOLYLALANINE

(75) Inventors: Robert L. Pollack, Philadelphia, PA (US); John C. Godfrey, Huntingdon Valley, PA (US); F. Warren Colvin, Eugene, OR (US)

(73) Assignee: AminoPath Labs, LLC, Portland, OR (US)

( * ) Notice: Subject to any disclaimer, the term of this patent is extended or adjusted under 35 U.S.C. 154(b) by 97 days.

This patent is subject to a terminal disclaimer.

(21) Appl. No.: 10/367,667

(22) Filed: Feb. 14, 2003

(65) Prior Publication Data

US 2004/0030154 A1 Feb. 12, 2004

Related U.S. Application Data

(63) Continuation-in-part of application No. 09/924,387, filed on Aug. 7, 2001, now Pat. No. 6,541,644, and a continuation of application No. 09/361,489, filed on Jul. 26, 1999, now abandoned, and a continuation of application No. 09/030,952, filed on Feb. 26, 1998, now Pat. No. 5,945,542.

(60) Provisional application No. 60/362,933, filed on Mar. 7, 2002.

(51) Int. Cl.
*C07D 209/20* (2006.01)

(52) U.S. Cl. .................. 548/497; 548/496; 210/661

(58) Field of Classification Search ................ 548/496; 210/661; 562/445
See application file for complete search history.

(56) References Cited

U.S. PATENT DOCUMENTS

| | | | |
|---|---|---|---|
| 3,019,232 A | 1/1962 | Sakurai et al. | |
| 4,639,465 A | 1/1987 | Pollack et al. | |
| 4,650,789 A | 3/1987 | Pollack | |
| 4,769,474 A | 9/1988 | Miyahara et al. | |
| 4,853,377 A | 8/1989 | Pollack | |
| 4,897,380 A | 1/1990 | Pollack et al. | |
| 4,956,471 A | 9/1990 | Ito et al. | |
| 5,057,615 A | 10/1991 | Kono et al. | |
| 5,070,208 A | 12/1991 | Yarita et al. | |
| 5,300,653 A | 4/1994 | Nozaki et al. | |
| 5,945,542 A | 8/1999 | Pollack et al. | |

FOREIGN PATENT DOCUMENTS

| | | |
|---|---|---|
| DE | 3326633 C1 | 1/1985 |
| JP | 61-189266 | 8/1986 |
| JP | 61-189267 | 8/1986 |
| JP | 61 249961 | 11/1986 |

OTHER PUBLICATIONS de Hollanda e Vasconcellos, A. M., et al., "Adsorption Chromatography of Phenylalanine," *Biotechnology and Bioengineering*, vol. 33, pp. 1324-1329, (Apr., 1989).
Fernstrom, J.D., "Dietary Effects on Brain Serotonin Synthesis: Relationship to Appetite Regulation," *American Journal of Clinical Nutrition*, vol. 42, pp. 1072-1082, American Society for Clinical Nutrition, (Nov., 1985).
Hartmann, E., "L-tryptophan: A Rational Hypnotic with Clinical Potential," *American Journal of Psychiatry*, vol. 134, pp. 366-370, (Apr., 1977).
Hoya et al., *Chemical Abstracts*, vol. 109, No. 190,865, 1988.
Lancaster Catalog, 1997-1999, p. 1724, 1997.
Lee, Kisay, et al., "Nonionic Adsorption of Aromatic Amino Acids on a Cation-Exchange Resin," *Reactive & Functional Polymers*, vol. 28, No. 1, pp. 75-80 (Dec. 1, 1995).
Moeller, F.G., et al., "Tryptophan Depletion and Aggressive Responding in Healthy Males," *Psychopharmacology*, vol. 126, pp. 97-103, Springer-Verlag, (1996).

(Continued)

*Primary Examiner*—Kamal A. Saeed
(74) *Attorney, Agent, or Firm*—Kolisch Hartwell, P.C.

(57) ABSTRACT

Processes for extracting amino acids from mixtures of amino acids, and compositions and mixtures formed therefrom. Applications include isolating natural L-β-3-indolylalanine (L-β-3) and providing natural or other amino acid mixtures enriched with the extracted L-β-3. The source of amino acids may include a natural source, such as enzymatic or other natural protein hydrolysates containing mixtures of free amino acids. The process includes contacting the mixture of amino acids with a resin or hydrophobic substance that is attractive to aromatic amino acids but not attractive to aliphatic amino acids to separate the aromatic amino acids from the rest of the mixture. This contacting may include agitating the mixture and hydrophobic substance to increase contact therebetween. The L-β-3 may then be separated from the monocylic amino acids by contacting the hydrophobic substance with an acid, and L-β-3 may be removed from the hydrophobic substance by contact with a base.

27 Claims, No Drawings

OTHER PUBLICATIONS

Møller, S.E., et al., "Aggression and Personality: Association with Amino Acids and Monamine Metabolites," *Psychological Medicine*, vol. 26, pp. 323-331, Cambridge University Press, (1996).

Murray, R.K., et al., "Biochemistry of Extracellular & Intracellular Communication," *Harper's Biochemistry*, 21st Ed., Section V., pp. 445-462, Appleton & Lange, Norwalk, Connecticut/San Mateo, California, (1988).

Schneider-Helmert, D., et al., "Evaluation of L-tryptophan for Treatment of Insomnia: A Review," *Psychopharmacology*, vol. 89, pp. 1-7, Springer-Verlag, (1986).

Seltzer, S., et al., "Alteration of Human Pain Thresholds by Nutritional Manipulation and L-Tryptophan Supplementation," *Pain*, vol. 13, pp. 385-393, Elsevier Biomedical Press, (1982).

Seltzer, S., et al., "The Effects of Dietary Tryptophan on Chronic Maxillofacial Pain and Experimental Pain Tolerance," *Journal of Psychiatric Research*, vol. 17, No. 2, pp. 181-186, Pergamon Press, Ltd., (1982/1983).

Sternbach, R.A., et al., "Effects of Altering Brain Serotonin Activity on Human Chronic Pain," *Advances in Pain Research and Therapy*, vol. 1, pp. 601-606, Eds. J.J. Bonica, et al., Raven Press, New York, (1976).

Vasconcellos, A.M.H., et al.,, "Adsorption of Phenylalanine from Casein Hydrolysates," *Applied Biochemistry and Biotechnology*, vol. 37, pp., 69-80, The Humana Press, Inc., (1992).

Weltzin, T.E., et al., "Acute Tryptophan Depletion and Increased Food Intake and Irritability in Bulimia Nervosa," *American Journal of Psychiatry*, vol. 152, pp. 1668-1671, (Nov., 1995).

Young, S.N., et al., "The Effect of Low Brain Serotonin on Mood and Aggression in Humans: Influence of Baseline Mood and Genetic Factors," *Recent Advances in Tryptophan Research*, Eds. G.A. Filippini et al., pp. 45-50, Plenum Press, New York, (1996).

English language abstract, Japanese Patent No. 63130580, 1988.

English-language abstract of Japanese Patent No. JP 61-189267, 1987.

ISOLATION OF NATURAL L-β-3-INDOLYLALANINE AND ENRICHMENT OF NATURAL ALIPHATIC AMINO ACID MIXTURES WITH NATURAL L-β-3-INDOLYLALANINE

RELATED APPLICATIONS

The present application is a continuation-in-part of and claims priority to similarly entitled U.S. patent application Ser. No. 09/924,387, which was filed on Aug. 7, 2001 now U.S. Pat. No. 6,541,644, and which is a continuation of U.S. patent application Ser. No. 09/361,489, which was filed on Jul. 26, 1999 now abandoned and which is a continuation of U.S. patent application Ser. No. 09/030,952, which was filed on Feb. 26, 1998 and issued on Aug. 31, 1999 as U.S. Pat. No. 5,945,542. The present application also claims priority to U.S. Provisional Patent Application Ser. No. 60/362,933, which was filed on Mar. 7, 2002. The complete disclosures of the above-identified patent applications are hereby incorporated by reference for all purposes.

FIELD OF THE INVENTION

The invention relates generally to the extraction of amino acids from mixtures of amino acids, such as naturally occurring mixtures of amino acids. Applications of the invention include the isolation of natural L-β-3-indolylalanine (L-tryptophan, or, as used herein, L-β-3) and the provision of amino acid mixtures enriched with natural L-β-3.

BACKGROUND OF THE INVENTION

In order for multicellular organisms to function, it is necessary for the cells of a body to communicate with each other. In this way, it is possible to coordinate responses as required to constantly adjust to a continually changing external and internal environment. This communication process is dependent on two operating systems: the nervous system in which signals or messages are transmitted, and hormones that are secreted and transported to adjacent or distant tissues. Both of these systems initiate specific physiological actions dependent on the particular type of cell that is activated.

The first step in the transmission of a brain signal is the synthesis of a chemical molecule called a neurotransmitter. Of the many brain neurotransmitters that have been identified, several are not synthesized de novo in nerve terminals, but rather are the result of a series of enzymatic reactions which modify a precursor molecule, usually an amino acid. After the molecules of the neurotransmitter have been biosynthesized, they are stored in the axon terminals of pre-synaptic nerve fibers in tiny membrane-bound sacs called synaptic vesicles which serve to protect the neurotransmitter molecules until they are used.

Serotonin is a neurotransmitter that the brain utilizes to send messages (electrical impulses) from one brain cell to another. Brain levels of serotonin have been shown to be involved in diverse physiologic processes, the most studied being sleep, appetite, mood, and pain threshold. Biochemical disturbances in the brain resulting in reduced levels of serotonin have been linked to insomnia, excessive appetite and weight gain, clinical depression, aggressiveness, and lowered pain threshold. The latter abnormality results in chronic, intractable pain that generally is refractory to treatment by conventional medications.

The neurotransmitter serotonin is synthesized in the brain from the amino acid L-β-3. L-β-3 cannot be made in the body. L-β-3 must be introduced into the body from an outside source, such as from protein in food or as a dietary supplement. Along with the other amino acids present in the blood stream (which are absorbed from the small intestine from hydrolytic digestive processes in the gastrointestinal tract), L-β-3 is carried to the brain. In the brain, a very selective process then takes place prior to the formation of serotonin.

In order for L-β-3 to be converted to serotonin, L-β-3 must first cross a separating mechanism that exists between the blood vessels in the brain and the brain proper. For L-β-3 to pass from the circulating blood through the blood/brain barrier, a transport mechanism in the form of a carrier protein is required. The primary function of this mechanism is to isolate L-β-3 from the majority of other amino acids circulating in the blood and then to transport L-β-3 across this selective blood/brain barrier into the brain. Thereafter, a two-step enzymatic process converts the L-β-3 first to 5-hydroxy-L-β-3 and then to serotonin.

However, L-β-3 is not the only amino acid carried by this transport mechanism. Five other amino acids, which may be termed large neutral amino acids (LNAAs), are carried as well. LNAAs include phenylalanine, tyrosine, leucine, isoleucine, and valine. L-β-3 not only has to compete with these LNAAs for access to the transport mechanisms, but also has a lower affinity for the carrier system than do the LNAAs. Of the five LNAAs, phenylalanine is the most tightly bound to the transport protein and is therefore exerts the greatest degree of competition with L-β-3 for the protein carrier site and subsequent passage across the blood/brain barrier. To complicate this situation further, L-β-3 in foods is present in lower amounts than the LNAAs, particularly in animal proteins. All of these factors converge to limit the amount of L-β-3 that gets through to the brain to be finally converted into serotonin.

It is known that dietary supplementation with L-β-3 increases the blood level of L-β-3 and facilitates the passage of L-β-3 across the blood/brain barrier into the brain. The increased amount of L-β-3 in the brain permits a greater amount of L-β-3 to be converted to serotonin. There are, however, numerous conditions that can interfere with and decrease the amount of L-β-3 that normally passes through the blood/brain barrier into the brain each day. The primary factor that controls the degree to which L-β-3 is transported across the blood/brain barrier is the ratio of L-β-3 to LNAAs present in the blood going to the brain. At a lower-than-normal L-β-3 to LNAA ratio, the number of molecules of L-β-3 present at the blood/brain barrier is less than normal. The LNAAs, which are normally present in larger numbers than L-β-3, then overwhelm the L-β-3 by monopolizing the majority of the transport carriers. Accordingly, even less L-β-3 passes across the blood/brain barrier and into the brain, as compared to the number of LNAAs that are passed across the barrier. In attempting to correct this improper L-β-3/LNAA ratio, it was found that increasing dietary protein intake in order to add more L-β-3 to the system can result, paradoxically, in an even greater derangement of the L-β-3/LNAA ratio because of the simultaneous greater intake of LNAAs over the intake of L-β-3.

One means by which the L-β-3/LNAA ratio abnormality can be treated is by the administration of L-β-3 without the accompanying presence of the LNAAs, especially without the presence of phenylalanine. This administration of L-β-3 serves to: increase the L-β-3 portion of the circulating L-β-3/LNAA ratio, increase the amount of L-β-3 which will be transported across the blood/brain barrier into the brain, increase the L-β-3 pool in the brain, and increase the rate of conversion of L-β-3 to serotonin.

Prior to 1989, L-β-3 was available to consumers as a dietary supplement and could be purchased freely. Studies on the oral administration of L-β-3 under proper dietary conditions that provided a supplementary intake of this particular amino acid showed that supplemental L-β-3 helped to correct an improper L-β-3/LNAA ratio in the brain. This increased level of brain L-β-3 directly produced an increased brain serotonin level that was associated with a reduction or elimination of serotonin-deficiency syndromes.

In the late 1980's, none of the L-β-3 available in nationally marketed preparations was produced in the United States. All of the L-β-3 used in the United States was imported from Japan. In 1989, the U.S. Food and Drug Administration (FDA) halted the importation and sale of L-β-3 in the U.S. as a result of a highly toxic contaminant that was found in batches of L-β-3 made by a bacterial fermentation process used to produce L-β-3. To date, the importation of L-β-3 into the U.S. for human consumption and the sale of such imported L-β-3 containing products has not resumed.

L-β-3 is the only substance (precursor) utilized by the body in a normal physiological manner to form serotonin and maintain normal brain serotonin levels. Medications used to maintain brain serotonin levels act by interfering with the normal sequence of serotonin metabolism, which can result in adverse side effects. A need exists for natural L-β-3 that is not obtained by a bacterial fermentation process, ensuring the absence of potentially toxic products that were produced by microorganisms synthesizing L-β-3 as part of their metobolic cycle.

SUMMARY OF THE INVENTION

The invention relates to L-β-3 as a naturally-occurring amino acid found in common proteins; as the amino acid naturally used by the body to produce serotonin in the brain; and as obtained simply and directly from natural proteins, thereby being free of biologically produced contaminants. The invention is directed generally to the extraction of amino acids from mixtures of amino acids, such as naturally occurring mixtures of amino acids.

Aspects of the invention include separation of the amino acid L-β-3-indolylalanine from a natural source of a mixture of amino acids, preferably enzymatic Or other natural protein hydrolysates containing mixtures of free amino acids; preparation of an amino acid fraction from the aforementioned L-β-3 and an amino acid mixture (obtained during the aforementioned separation) that is substantially or completely free of aromatic amino acids, particularly phenylalanine; and preparation of highly enriched mixtures of L-β-3 and one or more non-aromatic amino acids, i.e., mixtures having a concentration of L-β-3 in an amount greater than that which occurs naturally. The L-β-3 and amino acid mixtures containing L-β-3 may be used to provide dietary therapeutic supplements for increasing the production of serotonin within the brain, thereby decreasing or eliminating undesirable physiological conditions brought about by a decreased brain serotonin level.

DETAILED DESCRIPTION AND BEST MODE OF THE INVENTION

The invention is directed to providing processes and compositions based on compounds obtained by such processes, for the extraction of amino acids from mixtures of amino acids, including mixtures of naturally occurring amino acids. An application of the invention includes (1) the separation, as a group, of aromatic amino acids, including L-β-3, from an amino acid mixture, the mixture preferably being obtained by the hydrolysis of common proteins; (2) the removal of L-β-3 from the mixture of amino acids obtained in (1); and (3) producing mixtures of one or more non-aromatic amino acids with the recovered L-β-3 in various proportions. Components isolated or recovered in the process of the invention are provided in a form suitable for further use.

The invention includes a process whereby a mixture of natural amino acids containing substantially all of the natural amino acids (i.e., glycine, the L-forms of alanine, arginine, asparagine, aspartic acid, cysteine, glutamic acid, glutamine, histidine, hydroxyproline, L-β-3, isoleucine, lucine, lysine, methionine, phenylalanine, proline, serine, threonine, tyrosine, and valine) in the form of free amino acids is separated into three fractions containing, respectively, (a) substantially all of the non-aromatic amino acids originally present, i.e., alanine, arginine, asparagine, aspartic acid, cysteine (in equilibrium with the dimeric cystine), glutamic acid, glutamine, glycine, histidine, hydroxyproline, isoleucine, leucine, lysine, methionine, proline, serine, threonine, and valine; (b) the monocyclic aromatic amino acids phenylalanine and tyrosine; and (c) L-β-3, the only amino acid of the group that possesses as a part of its structure two fused aromatic rings. In applications, the process may further provide a range of mixtures of fraction (a) with fraction (c) while specifically eliminating fraction (b), which is deleterious to the desirable physiological actions of L-β-3. These mixtures including one or more aliphatic amino acids and L-β-3 are possessed of highly desirable physiological properties useful in the therapeutic relief of human suffering related to and caused, at least in part, by a relative deficiency of L-β-3. It is within the scope of the invention that the source mixture of amino acids may contain fewer than all of the natural amino acids.

In one embodiment, the present invention involves applying or exposing by contact a solution of phenylalanine, tyrosine, and L-β-3 in the presence of mixed aliphatic amino acids to a hydrophobic substance such that the mixed aromatic amino acids adsorb selectively to the hydrophobic substance and can thereafter themselves be selectively and sequentially desorbed. As an illustrative example, a natural amino acid-containing mixture, or source, preferably an enzymatic or other natural protein hydrolysate, is dissolved, and contacted with a hydrophobic substance in order that aromatic amino acids will be selectively attracted to the hydrophobic substance and aliphatic amino acids will be carried away in the fluid carrier. The hydrophobic substance is thereafter washed to remove residual non-aromatic or aliphatic amino acids, which, while having essentially no affinity for the hydrophobic substance, may be physically associated with, but not bound by attractive forces to, the hydrophobic substance. Examples of suitable wash solutions include water, such as deionized water, although others may be used.

The amino acid mixture or source will typically be dissolved in water and may be, for example, an enzymatic hydrolysate of casein. An enzymatic hydrolysate of soy protein is also useful and is highly preferred since it contains twice as much free L-β-3 as does casein hydrolysate. Other natural protein hydrolysates may also be used without departing from the scope of the invention. The particular hydrolysate used will depend on availability. The protein hydrolysate used can be "concentrated" in the sense that a higher amount of protein hydrolysate is present to the amount of water when put in solution as compared to conventional preparations. The protein hydrolysate is generally present in an amount of 1–30% by wt. of the aqueous solution containing the protein hydrolysate. A preferred range for the present invention is 5 to 16% by weight. Most food-acceptable protein sources contain L-β-3 at about 0.5 to 1.5% by weight of the contained protein. As applied to extracting L-β-3, the process described herein serves to concentrate the L-β-3 from these sources to a range of about at least 10 to 75%.

The hydrophobic substance may be, for example, a resin, or a reverse phase silica gel, so long as the substance has an attraction for aromatic rings of amino acids but little or no attraction to aliphatic amino acids at the natural pH of the solution. The attraction to the aromatic rings of amino acids is believed to be based on the polymeric resin having attractive van der Waals interaction due to the pi-electrons of the polymer with the pi-electrons of the aromatic rings of the amino acids. The hydrophobic substance may be a porous, wettable polymeric resin, such as a non-ionic cross-linked polystyrene. A preferred polymeric resin suitable for use in the present invention is a non-ionic cross-linked polystyrene such as sold under the name AMBERLITE® XAD-4 resin sold by Rohm & Haas Company. Other polymeric resins also sold by Rohm & Haas which are suitable for use include, but are not limited to, the following: AMBERLITE® XAD-16, AMBERLITE® XAD 1180, AMBERLITE® XAD-2000, AMBERLITE® XAD-2010, DIAION™ HP20, DIAION™ HP20SS, SEPABEADS™ SP20MS, AMBERCHROM® CG-71, AMBERCHROM® CG-161, AMBERCHROM® CG-300, AMBERCHROM® CG-1000, AMBERSORB® 563, AMBERSORB® 575, AMBERSORB® 348F, and AMBERSORB® 572. The hydrophobic substance is present in any suitable form. In experiments, particulate form, including the form of porous beads, has proven to be effective.

Although not required, the hydrophobic substance may be contained within a porous carrier or container, which is then exposed to an amino acid solution. The porous container may take any suitable form to contain the hydrophobic substance and to permit amino acids to permeate or otherwise flow into the container and interact with the hydrophobic substance. An example of a suitable container is a porous container through which the mixture of amino acids may flow, yet within which the resin or other hydrophobic substance is retained. An example of such a container is a mesh bag, such as a fine mesh nylon bag, although other containers may be used without departing from the scope of the invention.

After contacting the hydrophobic substance with the amino acid solution, the hydrophobic substance may be washed with water (such as deionized water, or another suitable wash agent) to remove any residual non-aromatic or aliphatic amino acids that, while having essentially no affinity for the resin or other hydrophobic substance, may be physically associated with but not bound by attractive forces to the hydrophobic substance. The hydrophobic substance is then washed (once or serially) to selectively desorb phenylalanine and tyrosine from the hydrophobic substance while leaving L-β-3 adsorbed to the hydrophobic substance. For example, the hydrophobic substance may be washed with an acid capable of selectively desorbing phenylalanine and tyrosine from the hydrophobic substance while leaving L-β-3 adsorbed to the hydrophobic substance. Suitable acids include, but are not limited to, acetic acid, formic acid, propionic acid, butyric or isobutyric acid, and other weak acids. Suitable acids include short chain aliphatic acids having molecular weights no greater than 88.10 daltons and a Ka in the range of $1.77 \times 10^{-4}$ and $1.34 \times 10^{-5}$ ($pK_a$ in the range of 3.75 and 4.87) at 25° C. The acids will typically be applied in dilute form. A preferred acid from the standpoint of function and economy is dilute acetic acid. The hydrophobic substance may then be washed with water or another suitable rinsing agent to remove residual acid.

Thereafter, the hydrophobic substance is washed with a suitable release agent to displace the L-β-3 from the hydrophobic substance. For example, the hydrophobic substance may be washed (once or serially) with a base to displace the L-β-3 from the hydrophobic substance. Suitable bases include, but are not limited to, ammonia (in the form of ammonium hydroxide), trimethylamine, triethylamine, $(CH_3)_2NH$, $(C_2H5)_2NH$, $CH_3NH_2$, $CH_3CH_2NH_2$, and other weak bases. Suitable bases include ammonia and short chain aliphatic primary secondary or tertiary amines having molecular weights no greater than 101.19 daltons and a $K_b$ in the range of $1.26 \times 10^{-3}$ and $1.8 \times 10^{-5}$ ($pK_b$ in the range of 2.90 and 4.74) at 25° C. The bases will typically be applied in dilute form. A preferred base from the standpoint of function and economy is dilute ammonium hydroxide. Some bases may leave a salt or other residue in the final product that may be removed later, for example, in an additional rinse step. The hydrophobic substance may be subjected to additional wash steps, such as with a 50—50 or other mixture of ethanol and water, to ensure full removal of all L-β-3 absorbed to the substance.

The L-β-3 may be purified from any impurities including residual acid, base, or salts by any suitable purification step. For example, when the acid or base forms weak salts with amino acids, as is the case with both acetic acid and ammonium hydroxide, the salts are typically very volatile and readily decompose upon gentle heating. Thus, in this case, because amino acids do not decompose upon gentle heating, the solutions can readily be heated, such as under vacuum, to remove water and either the acid (from the phenylalanine plus tyrosine fraction) or the base (from the L-β-3 fraction) leaving behind the free amino acids in substantially pure form. This evaporative concentration, when performed on the L-β-3-containing solution, provides a dry, non-hygroscopic powder while removing excess base. As other examples, the L-β-3 may be recovered by crystallization, filtration, or centrifugation.

The elutions with acid and base allow the L-β-3 first to be held to the hydrophobic substance while removing phenylalanine and tyrosine and, thereafter, isolating the L-β-3 from a major amount of other amino acids, as well as residual peptides, in the starting hydrolysate mixture. It is particularly advantageous to remove phenylalanine from L-β-3 since, as described above, phenylalanine is strongly competitive with L-β-3 in the key systems which transport L-β-3 to the brain.

The contacting and elutions described herein may be enabled through any suitable batch or flow-through mechanism. For example, the resin or other hydrophobic substance may be packed in a column or retained in a reservoir through which the liquids are passed. The reservoir may retain the hydrophobic substance in a packed configuration or in a loose configuration in which the substance may move freely Within the reservoir. As another example, a porous carrier containing the hydrophobic substance is placed inside a reservoir containing the amino acid solution. The reservoir is then agitated, by shaking, stirring, swirling, rotating or other mechanisms, to allow for rapid interaction between the hydrophobic substance and the contents of the reservoir. The reservoir may be emptied and serially refilled with the various other solutions, i.e. rinsing solutions, acidic solutions, basic solutions, etc., with the carrier remaining inside the reservoir. Alternatively, a series of reservoirs is used and the carrier is transported from one reservoir to another.

The invention is further understood and described by the following examples that serve to illustrate, but not limit, the present invention.

EXAMPLE 1

Fractionation of a Digest of Casein which Contains L-β-3

This example describes the general procedure for the preparation of the fractions containing (a) substantially all of the non-aromatic amino acids originally present in the source containing a mixture of natural amino acids, i.e., alanine, arginine, asparagine, aspartic acid, cysteine (in equilibrium with the dimeric cystine), glutamic acid, glutamine, glycine, histidine, hydroxyproline, isoleucine, leucine, lysine, methionine, proline, serine, threonine, and valine; (b) the monocyclic amino acids phenylalanine and tyrosine; and (c) L-β-3.

A glass column, having the dimensions of 1 cm (inner diameter) by 30 cm and containing approximately 24 grams of AMBERLITE® XAD-4 (a completely nonioftic crosslinked polystyrene adsorbent in the form of white insoluble beads having an average diameter of 0.30 to 0.45 mm), was prepared according to the resin manufacturer's (Rohm and Haas Company) general directions for carrying out the adsorptive separation of aromatic from non-aromatic organic compounds. Briefly, the column was loosely wet-packed by pouring a suspension of the resin beads in water into the column. The column was then arranged to backwash (bottom to top) with water at a rate sufficient to expand the apparent column volume by 50%. Backwash with water was continued for ten minutes. The flow was then stopped and the resin beads were allowed to settle under the influence of gravity only, in order to achieve uniform packing of the column. After passing approximately 25 ml of water in the downward direction, down-wash was continued with 108 ml of 91% (weight/volume, aqueous) isopropyl alcohol in 37.5 minutes. The alcohol wash was followed by a wash with 432 ml of water during 1.25 hours, at an approximate flow rate of 9.6 ml/min. The resin column thus prepared was ready for the adsorptive separation of the mixed, free amino acids.

The starting material for the adsorptive separation of the mixed free amino acids had the following characteristics: a refined, enzymatic hydrolysate of casein as a dry powder containing 80% free amino acids, the remainder being almost entirely residual peptides. In terms of amino acid composition, the hydrolysate contained 819.5 mg/g of non-aromatic amino acids, 40.9 mg/g of L-phenylalanine plus L-tyrosine, and 5.7 mg/g of L-β-3.

A clear solution of the above starting material was prepared from 7.800 g of the hydrolysate in 78 ml of water at room temperature. This solution was applied to the resin column in five portions over 20 minutes at a flow rate of 4.0 ml/min. Elution with plain water was continued until 341 ml of eluate was collected in 3 yellow fractions of 104 ml, 124 ml, and 113 ml. Evaporation to dryness of these first 3 fractions yielded, respectively, 6.578 g, 1.016 g, and 0.107 g. Thin layer chromatography (TLC) demonstrated that these 3 fractions contained only the non-aromatic amino acids, i.e., they contained no L-phenylalanine, L-tyrosine, or L-β-3. Elution was then continued with 150 ml of 2% acetic acid in water, followed by 150 ml of water, and four fractions totaling 287 ml were collected. On evaporation to dryness, the fractions contained, respectively, 70.1 mg, 27.2 mg, 22.6 mg, and 13.2 mg of substance which was shown by TLC to consist of L-phenylalanine, L-tyrosine, and a trace amount of L-β-3. Elution was then continued with 100 ml of 1.0 N ammonium hydroxide, followed by 75 ml of water. Two fractions, totaling 178 ml, were collected. On evaporation to dryness, these fractions yielded a total of 70.6 mg of substance. TLC revealed that only L-β-3 was present. Since the recovery of L-β-3 was substantially greater than that expected from the reported content of 5.7 mg/g in the starting material, it is clear that the reported, estimated contents of amino acids in the starting material is an approximation. Nevertheless, the total weight recovered in all fractions from this column, 7.805 g, was very close to the input of 7.800 g.

EXAMPLE 2

Scale-Up of Fractionation of an Enzymatic Digest of Casein

Employing a column of the same dimensions and prepared in the same manner with AMBERLITE® XAD-4 resin beads as in Example 1, 10.000 g of the same casein enzymatic hydrolysate was dissolved in 78 ml of water and applied to the column during 21 minutes, followed by elution with water at a flow rate of 3.6 ml/min. Fractions were collected as follows:

| Fraction No. | Color | Volume (ml) |
| --- | --- | --- |
| 1 | yellow | 133.2 |
| 2 | pale yellow | 99.0 |
| 3 | faint yellow | 101.9 |

The eluant was changed to 2% acetic acid in water, 155 ml, followed by elution with water, and the following fractions were collected, all at a flow rate of 3.6 ml/min:

| Fraction No. | Color | Volume (ml) |
| --- | --- | --- |
| 4 | none | 78.5 |
| 5 | none | 91.4 |
| 6 | none | 81.6 |
| 7 | none | 59.4 |

The eluant was changed to 100 ml of 1 N ammonium hydroxide, followed by elution with water at a flow rate of 4.0 to 4.2 ml/min, and the following fractions were collected:

| Fraction No. | Color | Volume (ml) |
| --- | --- | --- |
| 8 | pale straw | 123.3 |
| 9 | none | 45.0 |

Fraction No. 8 was reduced to a thick, pale-yellow syrup by vacuum evaporation at 98° C. To this was added 25 ml of water and the evaporation was repeated to remove the last of the ammonia. On standing for 48 hours at room temperature, the oily residue yielded large, fernleaf-shaped crystals of L-β-3, confirmed by TLC in parallel with pure, authentic substance. Fraction Nos. 8 and 9 together yielded a total of 46.9 mg of L-β-3. Fraction Nos. 4, 5, and 6 together yielded a total of 192 mg of substance which was. mostly L-phenylalanine with a lesser amount of L-tyrosine and a trace amount of L-β-3, as shown by TLC analysis.

EXAMPLE 3

Adsorptive Separation of L-Phenylalanine, L-Tyrosine, and L-β-3 from Non-Aromatic Amino Acids on a Batch Process 240 grams of AMBERLITEO® XAD-4 resin was successively pre-washed with 2.0 liters of water, 1.1 liter of 91% isopropyl alcohol, and 5.5 liters of water and then placed in a 1.5 liter beaker equipped with a mechanical stirrer. 78.00 grams of the amino acid mixture was dissolved in 780 ml of water and added to the beaker containing the resin. The mixture was stirred for 1.0 hour at room temperature (22° C.), at a rate sufficient to maintain the resin in a uniform suspension.

The resin was filtered off in a Buchner funnel equipped with a coarse grade of filter paper (Whatman #1). The yellow filtrate was identified as Filtrate No. 1 and stored under refrigeration for later use.

The resin was returned to the beaker, stirred with 250 ml of water for 15 minutes (a slightly longer time does not affect the process), and filtered. The pale yellow filtrate was identified as Filtrate No. 2 and refrigerated for later use.

The water Wash was repeated and the Filtrate No. 3 was refrigerated. The resin was returned to the beaker and stirred with 250 ml of 2% aqueous acetic acid for 15 minutes at room temperature. The resin was filtered off and the colorless filtrate was identified as Filtrate No. 4 and preserved under refrigeration for later use.

The resin was returned to the beaker and washed twice, 10 minutes per wash, with 240 ml portions of water, and filtered after each wash. These water washes were identified as Filtrate Nos. 5 and 6, and held under refrigeration for later use.

The resin was returned to the beaker and stirred for 15 minutes with 250 ml of 1 N ammonium hydroxide. The resin was separated by filtration and the pale straw-colored filtrate was identified as Filtrate No. 7.

The resin was returned to the beaker and washed twice, 10 minutes per wash, with 240 ml portions of water, filtering after each wash. The filtrates were identified as Filtrate Nos. 8 and 9, and held under refrigeration for later use.

As Filtrate No. 7 was expected to contain the major portion of the recoverable L-β-3, it was immediately vacuum-evaporated at 98° C., the residue twice re-dissolved in 25 ml portions of water and re-evaporated under vacuum to remove all of the ammonia. The fully dried off-white residue weighed 355 mg (445 expected) and was shown by TLC in parallel with a standard to be substantially pure L-β-3 with no more than a trace of L-phenylalanine and no L-tyrosine. When this sample was dissolved/suspended in 5.0 ml of water and refrigerated, it was converted to a crystalline mass over a period of several days. Filtration and drying provided 271.3 mg of substantially pure, crystalline product, L-β-13.

An aliquot of Filtrate No. 1 was vacuum-evaporated to dryness at 98° C. The weight recovered corresponded to a weight of 59.0 g in Filtrate No. 1. TLC revealed the presence of mixed aliphatic amino acids, no L-phenylalanine, no L-β-3, and a faint trace of L-tyrosine. Therefore the entire Filtrate No. 1 was spray-dried under vacuum and mild heat to produce a pale tan powder weighing (in total) 58.5 g and possessing a pleasant, slightly meaty flavor with a sweet background note.

Investigation of Filtrate No. 4 revealed that it contained 2.55 g of solids (dry) which, based upon TLC analysis, consisted of a mixture of L-phenylalanine and a relatively minor amount of L-tyrosine. No other amino acids were apparent in this product.

Finally, Filtrate No. 8 was investigated and found to contain 32 mg of L-β-3 (TLC).

EXAMPLE 4

13% L-β-3 Admixed with Aliphatic Amino Acids by Dry Compounding

A mixture of 13.0 g of L-β-3 and 87.0 g of spray-dried aliphatic amino acids (consisting of glycine and the L-forms of alanine, arginine, aspartic acid, cysteine, glutamic acid, histidine, isoleucine, leucine, lysine, methionine, proline, serine, threonine, and valine, obtained, for example, from Filtrate No. 1 of Example 3) was placed in a small ball-mill equipped with ceramic balls, and milled for 4.0 hours at ambient temperature. The resulting fine, light-tan powder was found to have a total nitrogen content of 13.1% and a pleasant, slightly meat-like odor and flavor.

EXAMPLE 5

25% L-β-3 Admixed with Aliphatic Amino Acids by Aqueous Compounding

As was noted in Example 3, Filtrate No. 7 was found to contain 355 mg of L-β-3 in 250 ml of solution and Filtrate No. 1 contained 58.5 g of mixed aliphatic amino acids in a volume of 780 ml. Therefore, in a fractionation experiment identical to that of Example 3, the entire Filtrate No.7, 240 ml, was combined with 14.2 ml of Filtrate No. 1 (which was calculated to contain 1065 mg of mixed aliphatic amino acids) and the entire solution evaporated to dryness under vacuum at 98° C. It was re-evaporated to dryness each time after 2 successive additions of 40 ml of water, until the condensate from the evaporation was neutral, showing that all of the ammonia had been displaced. The remaining dry solid, 1.32 g, was found on three successive analyses of samples taken randomly from the mixture to have total nitrogen content of 13.2%, 13.3%, and 13.3%. The total nitrogen content is noticeably greater than that of the starting material, probably because of the formation of ammonium salts of aspartic and glutamic acids in the mixed aliphatic amino acids during exposure to the excess ammonium hydroxide present in Filtrate No. 7.

EXAMPLE 6

135 milliliters of washed AMBERLITE® XAD-4 non-ionic resin was placed inside a fine mesh nylon bag. The bag was inserted into a 200-milliliter plastic tube. 45 grams of hydrolyzed casein powder was dissolved in 175 milliliters of water. The casein solution was added to the tube. The tube was attached to a horizontal stir motor and rotated slowly for two hours. The protein solution was drained and replaced by 125 milliliters of water. The water charge was repeated three more times. 125 milliliters of 2% acetic acid was added three times, followed by three charges of 125 milliliters of water. 125 milliliters of 1 N ammonium hydroxide was added twice. These ammonium hydroxide washes were combined as fraction #1. Final washes of 125 milliliters of 50% ethanol/water and water were combined as fraction #2. After removal of liquid, fraction #1 gave 800 milligrams of solids, and fraction #2 gave 400 milligrams. Fraction #1 was tan in color, and fraction #2 was a darker brown.

EXAMPLE 7

60 milliliters of AMBERLITE) XAD-4 non-ionic resin was placed in a fine mesh nylon bag. 32 grams of casein powder was dissolved in 250 milliliters of water. The resin bag was added to the protein solution in a 1000 milliliter beaker. The solution was stirred for one hour. The protein solution was poured off and replaced with the first water wash of 1000 milliliters. This was repeated with three more water washes of 1000 milliliters. Two 500 milliliter washes of 2% acetic acids were stirred for one hour each, followed by three 1000 milliliter Water washes for one hour each. 320 milliliters of 1 N ammonium hydroxide solution was stirred for one hour, followed by three 500 milliliter water washes. The final wash was 500 milliliters of 50% ethanol/water.

400 milligrams of light tan solid was isolated from the ammonium hydroxide and ethanol washes.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A process for isolating substantially pure L-β-3-indolylalanine (L-β-3) from a source of amino acids including L-β-3, the process comprising:
    contacting a porous container containing a hydrophobic substance being attractive to aromatic amino acids and having substantially no attraction to aliphatic amino acids with an aqueous solution of the source of amino acids;
    agitating the aqueous solution and the porous container to allow a substantial portion of the L-β-3 to adsorb to the hydrophobic substance and thereby produce a first solution containing aliphatic amino acids;
    separating the porous container from the aqueous solution;
    contacting the porous container with an acidic solution to produce a second solution containing any L-phenylalanine and L-tyrosine displaced from the hydrophobic substance, wherein the acidic solution includes an acid selected from one or more of a group consisting of acetic acid, formic acid, propionic acid, butyric acid, isobutyric acid, and acids having a molecular weight no greater than 88.10 daltons and a $K_a$ in the range of $1.77 \times 10^{-4}$ and $1.34 \times 10^{-5}$ at 25° C.;
    separating the porous container from the second solution; and
    contacting the porous container with a basic solution to displace L-β-3 from the hydrophobic substance and thereby produce a third solution containing L-β-3, wherein the basic solution includes a base selected from one or more of a group consisting of ammonia, short chain aliphatic primary, secondary or tertiary amines, trimethylamine, triethylamine, $(CH_3)_2NH$ $(C_2H_5NH, CH_3NH_2, CH_2CH_2NH_2$ and bases having a molecular weight no greater than 101.19 daltons and a $K_b$ in the range of $1.26 \times 10^{-3}$ and $1.8 \times 10^{-5}$ at 25° C.

2. The process of claim 1, further comprising the step of recovering L-β-3 from the third solution.

3. Substantially pure L-β-3 made by the process of claim 2.

4. The process of claim 2, wherein the step of recovering is performed by a process selected from one or more of a group consisting of separation by filtration, separation by centrifugation, separation by evaporation and separation by crystallization.

5. The process of claim 1, wherein the source of amino acids is selected from one or more of a group consisting of a protein hydrolysate of natural proteins, an enzymatic hydrolysate of casein and an enzymatic hydrolysate of soy protein.

6. The process of claim 1, wherein the hydrophobic substance includes a polymeric resin.

7. The process of claim 6, wherein the resin is selected from one or more of a group consisting of a porous resin, a non-ionic resin, a non-ionic porous resin, a non-ionic cross-linked polystyrene, a particulate-form resin, and a bead-form resin.

8. The process of claim 1, wherein the basic solution includes a base selected from one or more of a group consisting of ammonia, short chain aliphatic primary, secondary or tertiary amines, trimethylamine, triethylamine, $(CH_3)_2NH$, $(C_2 H_5)_2NH$, $CH_3NH_2$, $CH_2CH_2NH_2$ and bases having a molecular weight no greater than 101.19 daltons and a $K_b$ in the range of $1.26 \times 10^{-3}$ and $1.8 \times 10^{-5}$ at 25° C.

9. The process of claim 1, further comprising combining at least a portion of the first solution with at least a portion of the third solution.

10. A mixture of amino acids produced by the process of claim 9.

11. The process of claim 1, further comprising recovering the aliphatic amino acids from the first solution.

12. The process of claim 1, further comprising recovering the L-phenylalanine and L-tyrosine from the second solution.

13. The process of claim 1, further comprising washing the porous container with a wash solution containing water prior to at least one of the contacting steps.

14. The process of claim 13, further comprising washing the porous container with a wash solution containing water prior to all of the contacting steps.

15. The process of claim 13, wherein the wash solution further includes an alcohol.

16. The process of claim 1, wherein the porous container is adapted to retain the hydrophobic substance in a packed configuration.

17. The process of claim 1, wherein the porous container is adapted to retain the hydrophobic substance therein while enabling the hydrophobic substance to move freely within the container.

18. A process for obtaining amino acids from a mixture of amino acids, the process comprising:
providing an aqueous solution of a mixture of amino acids that includes L-β-3-indolylalanine (L-β-3);
contacting the aqueous solution with a hydrophobic substance to form a first solution comprising non-aromatic amino acids, wherein the hydrophobic substance is attractive to aromatic amino acids and has substantially no attraction to aliphatic amino acids;
eluding the hydrophobic substance with an acid to provide a second solution comprising monocyclic amino acids;
eluding the hydrophobic substance with a base to provide a third solution comprising L-β-3, and
recovering at least one of a group selected from the non-aromatic amino acids from the first solution, the monocyclic amino acids from the second solution, and the L-β-3 from the third solution.

19. The process of claim 18, wherein the mixture of amino acids is obtained from one or more of a group consisting of a protein hydrolysate of natural proteins, an enzymatic hydrolysate of casein and an enzymatic hydrolysate of soy protein.

20. The process of claim 18, wherein the hydrophobic substance includes a resin selected from one or more of a group consisting of a porous resin, a non-ionic resin, a non-ionic porous resin, a non-ionic cross-linked polystyrene, a particulate-form resin, and a bead-form resin.

21. The process of claim 18, wherein the acid is selected from one or more of a group consisting of acetic acid, formic acid, propionic acid, butyric acid, isobutyric acid, and acids having a molecular weight no greater than 88.10 daltons and a $K_a$ in the range of $1.77 \times 10^{-4}$ and $1.34 \times 10_{-5}$ at 25° C.

22. The process of claim 18, wherein the base is selected from one or more of a group consisting of ammonia, short chain aliphatic primary, secondary or tertiary amines, trimethylamine, triethylamine, $(CH_3)_2NH$, $(C_2H_5)_2NH$, $CH_3NH_2$, $CH_2CH_2NH_2$ and bases having a molecular weight no greater than 101.19 daltons and a $K_b$ in the range of $1.26 \times 10^{-3}$ and $1.8 \times 10^{-5}$ at 250° C.

23. The process of claim 18, wherein the step of recovering is performed by a process selected from one or more of a group consisting of separation by filtration, separation by centrifugation, separation by evaporation and separation by crystallization.

24. The process of claim 18 further comprising the step of combining at least a portion of the first solution with at least a portion of the third solution.

25. The process of claim 18, wherein the recovering step includes recovering the non-aromatic amino acids from the first solution.

26. The process of claim 18, wherein the recovering step includes recovering the monocyclic amino acids from the second solution.

27. The process of claim 18, wherein the recovering step includes recovering the L-β-3 from the third solution.

* * * * *

UNITED STATES PATENT AND TRADEMARK OFFICE
CERTIFICATE OF CORRECTION

| | |
|---|---|
| PATENT NO. | : 7,030,248 B2 |
| APPLICATION NO. | : 10/367667 |
| DATED | : April 18, 2006 |
| INVENTOR(S) | : Robert L. Pollack, John C. Godfrey and F. Warren Colvin |

Page 1 of 1

It is certified that error appears in the above-identified patent and that said Letters Patent is hereby corrected as shown below:

Column 12,
Lines 33-34, after "amines, trimethylamine, triethylamine," please delete
"$(CH_3)_2NH$ $(C_2H_5NH, CH_3NH_2, CH_2CH_2NH_2$ and" and insert
-- $(CH_3)_2NH, (C_2H_5)_2NH, CH_3NH_2, CH_2CH_2NH_2$ and -- therefor.

Column 12,
Line 62, after "$CH_3NH_2$," please delete "$CH_2CH_2NH_2$ and" and insert
-- $CH_2CH_2NH_2$ and -- therefor.

Column 13,
Line 32, before "the hydrophobic substance" please delete "eluding" and insert
-- eluting -- therefor.

Column 13,
Line 34, before "the hydrophobic substance" please delete "eluding" and insert
-- eluting -- therefor.

Column 14,
Line 13, after "in the range of $1.77 \times 10^{-4}$ and" please delete "$1.34 \times 10_{-5}$" and insert
-- $1.34 \times 10^{-5}$ -- therefor.

Column 14,
Line 18, after "$CH_3NH_2$," please delete "$CH_2CH_2NH_2$ and" and insert
-- $CH_2CH_2NH_2$ and -- therefor.

Column 14,
Line 20, after "and $1.8 \times 10^{-5}$ at" please delete "$250°$ C" and insert -- $25°$ C --therefor.

Signed and Sealed this

Eighteenth Day of July, 2006

JON W. DUDAS
*Director of the United States Patent and Trademark Office*